: US 11,202,987 B2
: Dec. 21, 2021

(12) United States Patent
Henson et al.

(54) MULTI-STAGE COMPRESSION AND COMPONENT REMOVAL

(71) Applicant: Honeywell International Inc., Morris Plains, NJ (US)

(72) Inventors: Phoebe Henson, Scottsdale, AZ (US); Stephen Yates, South Barrington, IL (US); Henry Claeys, Rancho Palos Verdes, CA (US); David Loeffelholz, Long Beach, CA (US)

(73) Assignee: Honeywell International Inc., Charlotte, NC (US)

(*) Notice: Subject to any disclaimer, the term of this patent is extended or adjusted under 35 U.S.C. 154(b) by 189 days.

(21) Appl. No.: 16/164,461

(22) Filed: Oct. 18, 2018

(65) Prior Publication Data

US 2020/0122084 A1 Apr. 23, 2020

(51) Int. Cl.
*B01D 53/26* (2006.01)
*C07C 1/12* (2006.01)
(Continued)

(52) U.S. Cl.
CPC ......... *B01D 53/265* (2013.01); *B01D 5/0039* (2013.01); *B01D 53/002* (2013.01);
(Continued)

(58) Field of Classification Search
CPC .... B01D 5/0039; B01D 53/002; B01D 53/22; B01D 53/229; B01D 53/26; B01D 53/265;
(Continued)

(56) References Cited

U.S. PATENT DOCUMENTS 3,276,679 A * 10/1966 Booth .................... B01D 45/14
494/36
4,362,540 A * 12/1982 Strahsner ............. B01D 50/004
96/359
(Continued)

FOREIGN PATENT DOCUMENTS

EP 2685190 A1 1/2014
EP 3366365 A1 8/2018
(Continued)

OTHER PUBLICATIONS

Modekurti, et al., "Design, dynamic modeling, and control of a multistage CO2 compression system," International Journal of Greenhouse Gas Control, Jul. 2017, accepted Mar. 9, 2017, pp. 31-45.
(Continued)

*Primary Examiner* — Jonathan Miller
*Assistant Examiner* — Gabriel E Gitman
(74) *Attorney, Agent, or Firm* — Shumaker & Sieffert, P.A.

(57) ABSTRACT

A gas compression system includes a system inlet to receive a gas stream containing a first component and a second component, a vapor system outlet to discharge the gas stream, and a plurality of compression stages coupled in series between the system inlet and the vapor system outlet. Each of the plurality of compression stages includes a compressor, a condenser coupled to the compressor, and a gravity-independent phase separator coupled to the condenser. The compressor is configured to receive the gas stream from either the system inlet or another of the plurality of compression stages and compress the gas stream. The condenser is configured to condense the second component from the gas stream. The gravity-independent phase separator is configured to remove the second component from the gas stream and discharge the gas stream to either the
(Continued)

system outlet or another of the plurality of compression stages.

20 Claims, 5 Drawing Sheets

(51) Int. Cl.
  *F04B 37/12* (2006.01)
  *F04B 39/06* (2006.01)
  *B01D 5/00* (2006.01)
  *B01D 53/00* (2006.01)

(52) U.S. Cl.
  CPC ............... *B01D 53/26* (2013.01); *C07C 1/12* (2013.01); *F04B 37/12* (2013.01); *F04B 39/064* (2013.01); *F25J 2230/04* (2013.01)

(58) Field of Classification Search
  CPC .......... B01D 2256/22; B01D 2256/245; B01D 2257/80; B01D 2258/06; B01D 2259/4508; B01D 2259/4575; C07C 1/12; F04B 37/12; F04B 39/064; F25J 2230/04
  See application file for complete search history.

(56) References Cited

U.S. PATENT DOCUMENTS

| | | | | |
|---|---|---|---|---|
| 4,452,676 | A * | 6/1984 | Birbara | C01B 32/05 205/628 |
| 5,250,091 | A * | 10/1993 | Nigsch | H01M 8/04156 55/490.2 |
| 5,352,272 | A | 10/1994 | Moll et al. | |
| 6,619,054 | B1 * | 9/2003 | Cargnelli | B01D 5/0021 62/317 |
| RE39,122 | E * | 6/2006 | Henderson | B01D 53/04 95/120 |
| 8,647,409 | B2 | 2/2014 | Hashi et al. | |
| 10,072,239 | B1 * | 9/2018 | Berberoglu | C12M 21/04 |
| 2006/0225386 | A1 * | 10/2006 | Brouwers | B01D 53/002 55/319 |
| 2009/0075219 | A1 * | 3/2009 | Vilagines | F23J 15/06 431/3 |
| 2010/0279181 | A1 | 11/2010 | Adams, II et al. | |
| 2010/0279191 | A1 | 11/2010 | Matsuura et al. | |
| 2010/0288121 | A1 * | 11/2010 | Antonio | B01D 53/261 95/41 |
| 2012/0009109 | A1 | 1/2012 | Wright et al. | |
| 2012/0153514 | A1 * | 6/2012 | Baxter | B01D 53/002 261/128 |
| 2012/0183457 | A1 * | 7/2012 | MacCallum | B01D 53/268 423/210 |
| 2012/0291630 | A1 | 11/2012 | Paragano et al. | |
| 2014/0033747 | A1 * | 2/2014 | Stallman | B01D 53/00 62/115 |
| 2014/0161698 | A1 | 6/2014 | Klimpel | |
| 2014/0326428 | A1 * | 11/2014 | Meirav | F28D 1/04 165/11.1 |
| 2015/0104290 | A1 * | 4/2015 | Dickson | F04D 17/10 415/1 |
| 2018/0056233 | A1 | 3/2018 | Henson et al. | |
| 2018/0056234 | A1 | 3/2018 | Weng et al. | |
| 2018/0243682 | A1 | 8/2018 | Isobe et al. | |
| 2018/0243685 | A1 | 8/2018 | Henson et al. | |
| 2018/0265993 | A1 | 9/2018 | Kamire et al. | |
| 2019/0047721 | A1 | 2/2019 | Rheaume et al. | |

FOREIGN PATENT DOCUMENTS

| | | |
|---|---|---|
| WO | 2011010111 A2 | 1/2011 |
| WO | 2016108731 A1 | 7/2016 |

OTHER PUBLICATIONS

"Normal Gravity Testing of a Microchannel Phase Separator for Insitu Resource Utilization," NASA, Jun. 2001, 24 pp.
"A Preliminary Assessment of Phase Separator Ground-Based and Reduced-Gravity Testing for ALS Systems," NASA, Feb. 2006, 25 slides.
Ellis, "The Tangential Velocity Profile and Momentum Transfer within a Microgravity Vortex Separator," Dec. 2006, 146 pp.
Kang, "Investigation of Passive Cyclonic Gas-Liquid Separator Performance for Microgravity Applications," Jan. 2017, 168 pp.
Thomas, et al., "Development of the Static Phase Separator," NASA, Jan. 2008, 8 pp.
Matteau, et al. "A Two-Phase Fluid Pump for Use in Microgravity Enviroments," Jul. 1999, 8 pp.
Yates et al., "A Closed-Loop CO2 and Humidity Recovery System for Deep Space Missions," 47th International Conference on Environmental Systems, ICES, Jul. 16-20, 2017, 16 pp.
U.S. Appl. No. 16/551,368, by Honeywell International Inc. (Inventors: Rebecca Kamire et al.), filed Aug. 26, 2019.
Wu et al., "Development of a passive phase separator tor space and earth applications," Journal of Separation and Purification Technology, Elsevier, published online Aug. 7, 2017, 9 pp.
Extended Search Report from counterpart European Application No. 19203120.1, dated Apr. 29, 2020, 7 pp.
Response to Extended Search Report dated Apr. 29, 2020, from counterpart European Application No. 19203120.1, filed May 13, 2020, 12 pp.
Office Action from U.S. Appl. No. 16/551,368, dated Aug. 20, 2021, 9 pp.

\* cited by examiner

MULTI-STAGE COMPRESSION AND COMPONENT REMOVAL

TECHNICAL FIELD

The present disclosure relates to systems and techniques for, in some examples, processing air for contaminant removal systems.

BACKGROUND

Life support systems and in situ resource utilization systems may compress and condense humid gases to produce a dry gas stream and liquid water. For example, in a carbon dioxide ($CO_2$) and humidity removal system, $CO_2$ and humidity may be removed through absorption by a sorbent, then subsequently desorbed at a lower pressure, and pressurized to a level around ambient pressure. The pressurized $CO_2$ may be sent to a $CO_2$ reduction/Sabatier system in which the $CO_2$ may be reacted with hydrogen to produce water vapor and methane gas, followed by subsequent pressurization of the methane to well above ambient pressure and drying of the methane for storage as fuel. To pressurize each of the $CO_2$ and methane gas streams, the respective gas stream may be compressed and cooled before water is removed from the gas stream.

SUMMARY

The disclosure describes systems and methods for efficiently compressing a gas stream using multistage compression and condensable component removal.

According to some examples of the disclosure, a compression system may utilize multiple stages, each stage having compression, condensation/cooling, and component removal, to efficiently compress and dry a gas stream by removing a condensable component from the gas stream. Multiple compression stages may be aligned in series between a gas stream inlet and a gas stream outlet. Each compression stage includes a compressor to compress the gas stream, a condenser to cool and/or condense a condensable component, such as water, from the gas stream, and a gravity-independent phase separator to remove the condensed component from the gas stream and discharge the gas stream to either the gas stream outlet or another of the compression stages. The use of gravity-independent phase separators enables the compression system to remove the condensable component under abnormal gravity environments, such as a partial gravity or microgravity environment found in outer space. Removal of the condensable component in multiple stages of compression may produce a gas stream that contains less of the component in later compression stages of the system. As a result, the systems and techniques discussed herein may utilize less power for compression and cooling than multistage compression systems that do not remove the component at each stage of compression.

In this way, the gas compression and component removal systems described herein may operate with reduced power, volume, and mass compared to a system that does not remove water in each compression stage. For example, when compressing gas streams, especially those with a high concentration of the component, the condensation and removal of the component in between the earlier stages of a vacuum pump/compressor may significantly reduce the load on the later stages of the vacuum pump/compressor. As another example, the removal of the component in between stages may reduce the total amount of gas that must be compressed at later stages. As yet another example, the lower temperature of the gas after condensation may decrease the volume of the gas that must be compressed at later stages even further and/or allow for a more isothermal compression, thus decreasing the total work required. Some examples of the gas compression and component removal system may also have improved reliability since removal of the component in between the stages removes a common failure mode of condensed component forming within the compressor, and since the cool and controlled operating temperature of the compression stages reduces stress on mechanical parts.

In some examples, the disclosure describes a gas compression system that includes a system inlet, a vapor system outlet, a liquid system outlet, and a plurality of compression stages coupled in series between the system inlet and the system outlet. The system inlet is configured to receive a gas stream containing a first component and a second component. The vapor system outlet configured to discharge the gas stream. Each of the plurality of compression stages includes a compressor, a condenser coupled to the compressor, and a gravity-independent phase separator coupled to the condenser. The compressor is configured to receive the gas stream from either the system inlet or another of the plurality of compression stages and compress the gas stream. The condenser is configured to cool the gas stream and condense the second component from the gas stream. The gravity-independent phase separator is configured to remove the second component from the gas stream and discharge the gas stream to either the vapor system outlet or another of the plurality of compression stages.

In some examples, the disclosure describes a method that includes receiving, by a gas compression system, a gas stream containing a first component and a second component; compressing, by a plurality of compression stages of the gas compression system, the gas stream; and discharging, by the gas compression system, the gas stream. The compression stages of the plurality of compression stages are coupled in series between the system inlet and the vapor system outlet. Each of the plurality of compression stages comprises compressing, by a compressor, the gas stream; condensing, by a condenser coupled to the condenser, the second component from the gas stream; removing, by a gravity-independent phase separator coupled to the condenser, the second component from the gas stream; and discharging, by the gravity-independent phase separator, the gas stream.

In some examples, the disclosure describes a non-transitory computer-readable storage medium storing instructions that, when executed, cause a processor to control a plurality of compression stages of a gas compression system to compress a gas stream containing a first component and a second component and remove the second component from the gas stream. The compression stages of the plurality of compression stages are coupled in series between a system inlet configured to receive the gas stream and a vapor system outlet configured to discharge the gas stream. The instructions, when executed, further cause the processor to, for each of the plurality of compression stages, cause a compressor to receive the gas stream from either a system inlet or another of the plurality of compression stages and compress the gas stream, cause a condenser to condense the second component from the gas stream, and cause a gravity-independent phase separator to remove the second component from the gas stream and discharge the gas stream.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

DETAILED DESCRIPTION

Figure 1A:
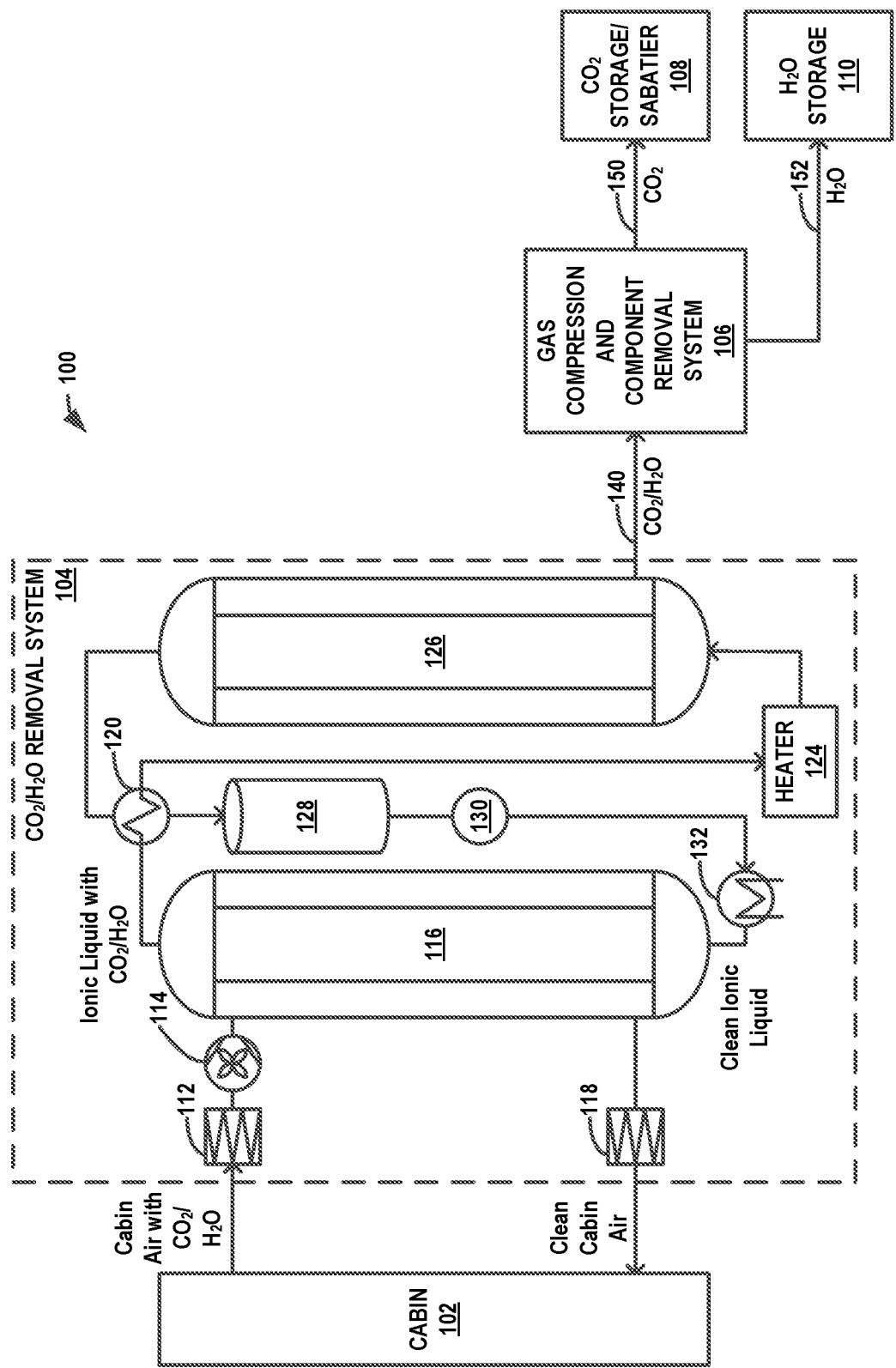
FIG. 1A is a diagram illustrating an example system for removing carbon dioxide and humidity from a controlled environment.

Gas compression and component removal systems discussed herein may be used to compress a gas stream and remove a condensable component from the gas stream. In some examples, the gas compression and component removal systems may be used to compress and remove water from carbon dioxide in an environmental control system. For example, in a resource-limited environment such as a spacecraft, carbon dioxide and water may be recycled to produce oxygen gas, water, methane, and a variety of other compounds used in life support systems. FIG. 1A is a diagram illustrating an example system 100 for removing carbon dioxide and humidity from a controlled environment. System 100 includes a cabin 102 that includes the controlled environment. Cabin 102 may include, but is not limited to, a spacecraft cabin, a submarine cabin, an aircraft cabin, and the like.

System 100 includes a carbon dioxide/water ($CO_2/H_2O$) removal system 104. $CO_2/H_2O$ removal system 104 may be configured to receive cabin air from cabin 102, remove contaminants, including water and carbon dioxide, from the cabin air, and discharge clean cabin air to cabin 102. Cabin air may be fed through a dust filter 112 to filter dust and particulates. Blower 114 may feed the filtered cabin air into a hollow fiber membrane scrubber 116. Scrubber 116 may be configured to remove carbon dioxide, water, and other contaminants using a sorbent; in the example of FIG. 1A, an ionic liquid sorbent is used. Scrubber 116 may discharge the clean cabin air through a final filter 118 back to cabin 102. The clean cabin air may have lower concentrations of carbon dioxide and water than the contaminated cabin air, such as below a target limit.

Ionic liquid sorbent with carbon dioxide and water may be discharged from scrubber 116 through a heat exchanger 120 and heater 124 into a hollow fiber membrane stripper 126. Stripper 126 may be configured to remove the carbon dioxide and water from the ionic liquid sorbent and discharge the ionic liquid sorbent through heat exchanger 120 into a clean ionic liquid storage tank 128. A pump 130 may feed the clean ionic liquid through a cooler 132 back into scrubber 116 for further removal of carbon dioxide and water from the cabin air.

$CO_2/H_2O$ removal system 104 may be configured to discharge a gas stream containing the removed $H_2O/CO_2$ to a gas compression and component removal system 106, as will be described further below. Gas compression and component removal system 106 may be configured to receive carbon dioxide and water through a system inlet 140, compress and discharge carbon dioxide through a vapor system outlet 150 to a carbon dioxide storage/Sabatier system 108, and separate and discharge water through a liquid system outlet 152 to a water storage system 110. Carbon dioxide storage/Sabatier system 108 may be configured to store the carbon dioxide, react the carbon dioxide with hydrogen gas to produce water and methane, or perform some other post-removal function. Water storage system 110 may be configured to store water, recycle water into $CO_2/H_2O$ removal system 104, such as by using a water vaporizer fed to stripper 126 to increase an efficiency of stripper 126, or perform some other post-removal function.

Further operation of system 100, including alternative configurations of system 100, may be found in co-pending patent application Ser. Nos. 15/896,150 and 15/896,156, incorporated by reference in their entirety herein. For example, $CO_2/H_2O$ removal system 104 may include a membrane dehumidifier between cabin 102 and scrubber 116.

For the carbon dioxide removed from $CO_2/H_2O$ removal system 104 to be stored or recycled, gas compression and component removal system 106 may remove nearly all water from the gas stream discharged from gas compression and component removal system 106. In a life support application, a large amount of water may be present in the gas stream received by system 106. For example, the concentration of water in this gas stream may be much higher than that of carbon dioxide. A safe partial pressure for carbon dioxide in a space vessel might be 2 torr. If the relative humidity in cabin 102 is 50%, and the pressure of cabin 102 is 760 torr, then the partial pressure of water will be 10.6 torr. As such, in the gas stream coming from stripper 126, the ratio of water to carbon dioxide would then be 5.3:1. If water is used to help strip the carbon dioxide in stripper 126 (not shown), then the ratio may be even higher. Thus, system 106 may receive streams that are mostly water. Carbon dioxide storage/Sabatier system 108 may require a water concentration of less than 2% to react hydrogen gas with carbon dioxide. A typical carbon dioxide compression and water removal system may utilize a single compressor, condenser, and water separator in series to compress the gas stream and condense and remove water from the gas stream. This system is often large and heavy, and may require significant power due to the amount of gas to be compressed.

Further, such a system may be unreliable, as water in the gas stream travels through each stage of compression before being removed, leading to higher temperatures and possible entrainment.

Figure 1B:
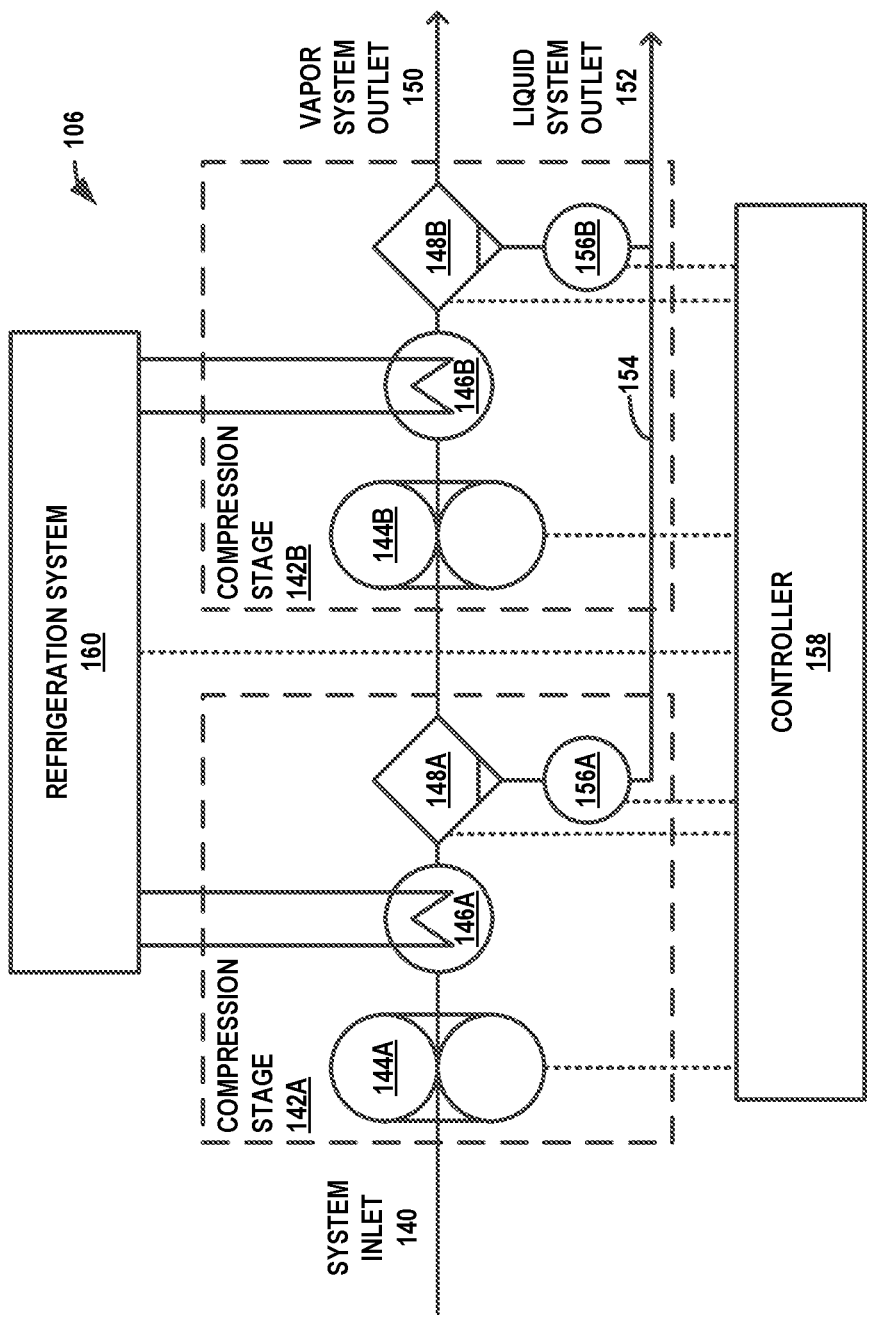
FIG. 1B is a diagram illustrating an example gas compression and component removal system of FIG. 1A for compressing a gas stream and removing a component from the gas stream using multi-stage compression and multi-stage gravity-independent phase separation.

According to some examples of the disclosure, gas compression and component removal systems discussed herein, such as gas compression and component removal system 106, may remove the component at multiple stages of a multi-stage compression system using gravity-independent phase separators. FIG. 1B is a diagram illustrating an example gas compression and component removal system 106 of FIG. 1A for compressing a gas stream and removing a condensable component from the gas stream using multi-stage compression and multi-stage gravity-independent phase separation.

The gas stream received by gas compression and component removal system 106 may be a gas mixture that includes at least a first component and a second component. Each of the first and second components may be a collection of one or more chemical species. The second component may include one or more chemical species that may condense due to changes in temperature and/or pressure conditions in various compression stages of gas compression and component removal system 106, while the first component may include one or more chemical species that may not substantially condense (i.e. condense in trace amounts or less) under these conditions, and thus undergo compression through the various compression stages of gas compression and component removal system 106. As such, while the gas stream is described as having a first component and a second component, the gas stream received at system inlet 140, the gas stream discharged at vapor system outlet 150, and/or the liquid discharged at liquid system outlet 152 may have any number or composition of chemical species, including overlapping chemical species.

While system 106 is shown in FIG. 1A as compressing carbon dioxide and removing water in a carbon dioxide and humidity removal system 100, system 106 may be used to compress and remove a variety of condensable components from a variety of gases. Gases that may be used include, but are not limited to, hydrocarbons, such as refrigerant gases; methane; air; and the like. Condensable components that may be removed include, but are not limited to, water; ammonia; and the like. For simplicity, FIGS. 1B, 2A-2C, 3, and 4 will be described for a second component of water removed from a gas stream that includes a first component and the second component. However, it will be understood that a variety of condensable components may be removed from a variety of gases and gas mixtures using the systems described herein.

As one example, a methane compression and water removal system may be included in carbon dioxide storage/Sabatier system 108 to remove water vapor from methane produced in a Sabatier process. For example, in a Sabatier process of carbon dioxide storage/Sabatier system 108, the carbon dioxide gas stream discharged from system 106 may be reacted with hydrogen to produce water and methane, followed by subsequent pressurization of the methane to well above ambient pressure and drying of the methane for storage as fuel. The resulting methane may be highly compressed to form methane for rocket fuel, while the resulting water may be stored and/or used for drinking water. In this way, systems that utilize the gas compression and water removal systems discussed herein may be approximately closed-loop.

As another example, an air compression and water removal system may be included as part of an environmental control system of an aircraft. For example, pressurized cabin air may be supplied from bleed air from the aircraft engines. By recycling cabin air using the air compression and water removal system, the amount of bleed air may be reduced, thereby reducing fuel consumption. As yet another example, an air compression and water removal system may be included as part of an environmental control system of a submarine, such as to reduce a load on water supply and/or carbon dioxide removal systems. Outside of environmental control systems and/or life support systems, an air compression and water removal system may be included as part of a power plant to capture carbon dioxide, compress and dry methane, and isolate water.

Referring to FIG. 1B, system 106 includes a system inlet 140, a vapor system outlet 150, and a liquid system outlet 152. System inlet 140 is configured to receive a gas stream at a system inlet pressure. Vapor system outlet 150 is configured to discharge the gas stream from system 106 at a vapor system outlet pressure. In some examples, system inlet 140 receives the gas stream at pressure less than 100 torr and vapor system outlet 150 discharges the gas stream at a pressure greater than the system inlet pressure and less than 10,000 torr. For example, for gas streams from a carbon dioxide and water removal system, such as carbon dioxide and water removal system 104, the system inlet pressure may be a low pressure to generate a vacuum in the stripper to remove the carbon dioxide and water from the ionic liquid sorbent, while the vapor system outlet pressure may be a pressure greater than about 1000 torr. In the examples of FIGS. 1A and 1B, system 106 may be configured to receive a gas stream containing carbon dioxide and a first concentration of water and discharge a gas stream containing carbon dioxide and a second concentration of water that is lower than the first concentration of water. For example, the gas stream received at system inlet 140 may have a water concentration greater than approximately 20% and less than approximately 90%, while the gas stream discharged at vapor system outlet 150 may have a water concentration less than approximately 10%. Liquid system outlet 152 is configured to discharge water from a liquid discharge line, as will be discussed further below. In some examples, system 106 may be configured to discharge a ratio of a water concentration of the gas stream received by system 106 to a water concentration of the gas stream discharged by system 106. For example, the gas stream received at system inlet 140 may have a water concentration greater than approximately 20% and the gas stream discharged at vapor stream outlet 150 may have a water concentration less than approximately 10%, such that a ratio may be greater than approximately 2.

System 106 includes a plurality of compression stages coupled in series between system inlet 140 and vapor system outlet 150. In the example of FIG. 1B, system 106 includes two compression stages 142A and 142B (collectively referred to as "compression stages 142"). However, any number of compression stages greater than a single compression stage may be used. The number of compression stages in system 106 may be selected based on a variety of factors that may include, but are not limited to: a system pressure ratio between the vapor system outlet pressure and the system inlet pressure; a power efficiency of system 106; a complexity of system 106; a type and/or design of pumps used in system 106; characteristics of gas species in the gas stream; a water concentration of vapor system outlet 150; a flowrate of water from liquid system outlet 152; and the like.

Each of the plurality of compression stages 142 may be configured to compress the gas stream and, optionally, cool the gas stream and/or remove water from the gas stream. For example, water condensation from the gas stream may be a function of pressure of the gas stream and water concentration in the gas stream such that, while the plurality of compression stages 142 remove water as a whole, some individual compression stages may not remove water for a particular set of characteristics of the gas stream. As water is removed from the gas stream, the amount of water, and thus gas, in the gas stream decreases. As a result, each subsequent compression stage may use less power to compress the smaller volume of gas, may have a smaller volume, and/or may have a smaller weight. Additionally or alternatively, as water is condensed from the gas stream, the temperature of the gas stream decreases. As a result, each subsequent compression stage may have a smaller volume, may allow for a more isothermal compression, which may use less power to compress the gas stream, and/or may have reduced stress on components, such as bearings of compressors.

Additionally or alternatively, the weight of the plurality of compression stages 142 may be reduced. Removing the water in multiple stages, rather than a single end stage, enables the use of a number of compressors that have an overall smaller weight than a single large compressor used in the single stage design. This may be particularly true for gas streams that have a high concentration of water, since as the compressors for the latter compression stages may be significantly smaller due to the greater amount of gas removed in prior compression stages.

Each of compression stages 142 includes a respective compressor 144A or 144B (collectively referred to as "compressors 144"), a respective condenser 146A or 146B (collectively referred to as "condensers 146"), and a respective gravity-independent phase separator 148A or 148B (collectively referred to as "phase separators 148"). As arranged in the example of FIG. 1B, a respective one of condensers 146 is coupled to one of compressors 144, and a respective one of phase separators 148 is coupled to one of condensers 146. However, an order or composition of the components of each of compression stages 142 may be different. For example, a condenser-phase separator-compressor configuration may be used, or a compressor-integrated condenser/phase separator configuration may be used. While compression stages 142 are shown in FIG. 1B as having the same equipment in each compression stage, different compression stages may utilize different types of one or more of compressors 144, condensers 146, and/or gravity independent phase separators 148. For example, a phase separator having a higher throughput but lower degree of liquid removal may be used at an earlier stage, while a phase separator having a lower throughput but higher degree of liquid removal may be used at a later stage.

Each of compressors 144 is configured to receive the gas stream from either system inlet 140 or another of the plurality of compression stages 142 at a compressor inlet pressure and compress the gas stream to a compressor outlet pressure. In the two-stage example of FIG. 1B, compressor 144A may receive the gas stream from system inlet 140 and compressor 144B may receive the gas stream from phase separator 148A. Due to compression of the gas stream, an outlet pressure and temperature of each of compressors 144 may be higher than an inlet pressure and temperature, while an outlet volumetric flow rate of each of compressors 144 may be lower than an inlet volumetric flow rate of each of compressors 144. A variety of compressors may be used for compressors 144 including, but not limited to, centrifugal compressors, positive displacement compressors, and the like. In some examples, compressors 144 are driven by a same axis. For example, each of compressors 144 may be coupled to a common shaft that drives the compressors, such that control of compressors 144 may be simplified or a weight of the compressors may be reduced.

Each of condensers 146 is configured to cool the gas stream and condense water from the gas stream. For example, each of condensers 146 may be coupled to a refrigeration system 160 or other cooling system that circulates a cooling medium to cool the gas stream. Due to cooling and/or condensation of water from the gas stream, an outlet condenser temperature of the gas stream may be lower than an inlet condenser temperature of the gas stream. A variety of condensers may be used for condensers 146 including, but not limited to, shell and tube heat exchangers, plate-fin, surface coolers, heat pipes, thermoelectric devices, cooling jackets, and the like. While shown as a separate unit, in some examples, condensers 146 may be integrated with at least one of compressors 144 and/or phase separators 148 into a single unit. For example, condensers 146 may be cooling jackets thermally coupled to at least one of compressors 144 and/or phase separators 148.

System 106 may operate independent of the gravity environment in which system 106 is located. Such gravity environments may be different from than typical gravity conditions on Earth. These abnormal gravity environments may include microgravity environments, such as such as orbiting satellite or space station environments; low or partial gravity environments that have a fraction of the surface gravity of Earth, such as environments of Mars or Earth's moon; turbulent and/or negative acceleration environments, such as airplanes or ships; high G environments, such as rockets or a spacecraft at the end of a launching rocket, in which orientation with the G force is not controllable; and the like. As such, condensers that rely on gravity for phase separation may not adequately remove water from a gas stream. For example, condensed water may continue to be entrained in the gas stream or may return to water vapor due to heat created during compression. If this water is not removed, it may cause pitting of compressor blades, wear on compressor bearings, and other equipment problems. Even gas compression and water removal systems that do operate in gravity environments may not achieve adequate separation from condensers that rely on gravity for phase separation, as such systems may require a high degree of water removal, may be unstable (e.g., aircraft), or may have a high throughput with limited residence time for settling or baffling.

To remove condensed water from the gas stream, system 106 may utilize gravity-independent phase separators 148. A gravity independent phase separator may be any phase separator capable of removing water from a gas stream without the use of gravity. For example, a phase separator that uses gravity may still be gravity-independent if the phase separator includes a mechanism that can remove water in a microgravity environment. Gravity-independent phase separators 148 may utilize a variety of mechanisms to remove water including, but not limited to, centrifugal forces, capillary forces, membranes, and electrostatic forces.

Each of gravity-independent phase separators 148 is configured to remove the component from the gas stream and discharge the gas stream to either vapor system outlet 150 or another of the plurality of compression stages 142. For example, phase separator 148A may discharge the gas stream to compressor 144B and phase separator 148B may discharge the gas stream to vapor system outlet 150. Due to this water removal, an amount of liquid discharged in the gas stream from each of phase separators 148 may be lower than an amount of water received in the gas stream for each of phase separators 148. This continuous removal of water in each compression stage 142 may reduce a load or wear on subsequent compression stages 142. A variety of gravity-independent phase separators may be used for gravity-independent phase separators 148 including, but not limited to, static phase separator, capillary phase separator, membrane phase separators, centrifugal/rotary separators, and the like. Further operation of phase separators 148 will be described in FIGS. 2A-C below. Depending on the amount of water that must be removed, one or more of phase separators 148 may be integrated into one of condensers 146 to reduce size further.

Each phase separator 148 is coupled to a liquid discharge line 154 and configured to discharge the water from the gas stream to liquid discharge line 154. Liquid discharge line 154 may be coupled to liquid system outlet 152. In the example of FIG. 1B, each of the plurality of compression stages further comprises a pump 156A or 156B (collectively referred to as "pumps 156") coupled to liquid discharge line 154. Each of pumps 156 may be configured to discharge the water from liquid discharge line 154 to liquid system outlet 152. Additionally, pumps 156 may create a vacuum or suction that assists in removing water from phase separators 148. In some examples, pumps 156 may be integrated with phase separators 148. For example, phase separators 148 may be rotary phase separators, such that pumps 156 may act as phase separators 148.

System 106 includes controller 158. Controller 158 may be configured to receive measurement from components of system 106 and/or control components of system 106. In the example of FIG. 1B, controller 158 is communicatively coupled to compressors 144, pumps 156, and refrigeration system 160, such that controller 158 may send control signals to any of compressors 144, pumps 156, and refrigeration system 160. For example, controller 158 may control a pumping speed of each of compressors 144, a water removal speed of pumps 156, and a cooling temperature (e.g., a condenser outlet temperature) of condensers 146. Controller 158 may include any of a wide range of devices, including control circuitry, processors (e.g., one or more microprocessors, one or more application specific integrated circuits (ASICs), one or more field programmable gate arrays (FPGAs), or the like), processing circuitry, one or more servers, one or more desktop computers, one or more notebook (i.e., laptop) computers, one or more cloud computing clusters, or the like. Further operation of controller 158 will be described in FIG. 3.

Figure 2A:
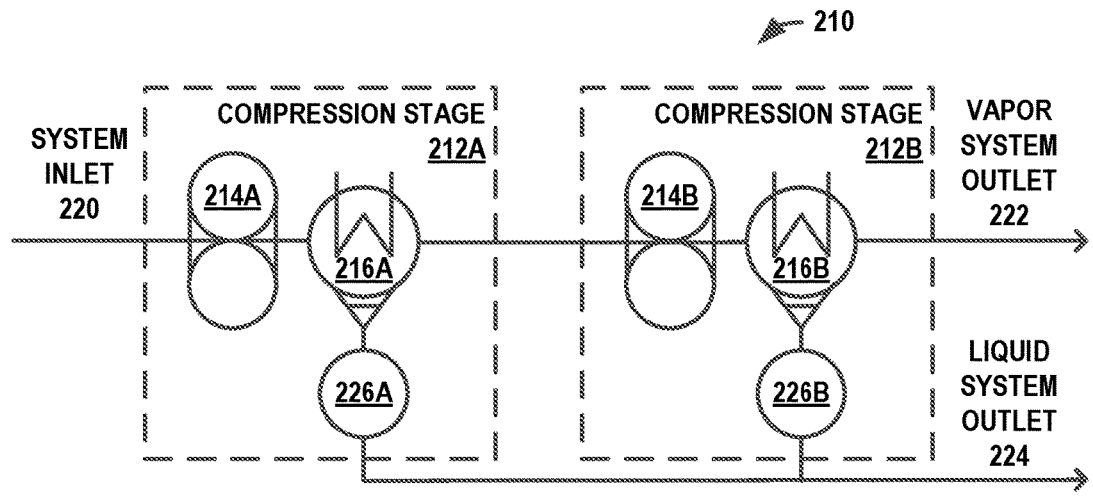
FIG. 2A is a diagram illustrating an example gas compression and component removal system for compressing a gas stream and removing a component from the gas stream using multi-stage compression and multi-stage, gravity-independent static phase separation.

In some examples, a gas compression and water removal system may utilize static phase separation to remove water from the gas stream. Static phase separation may be any phase separation that does not use moving parts. For example, static phase separation may be free of moving parts, such that reliability may be high, power may be low, external power may not be required, and/or heat generation may be low. FIG. 2A is a diagram illustrating an example gas compression and water removal system 210 for compressing a gas stream and removing water from the gas stream using multi-stage compression and multi-stage static phase separation. System 210 includes a system inlet 220, a vapor system outlet 222, a liquid system outlet 224, a first compression stage 212A, and a second compression stage 212B. Each of first compression stage 212A and second compression stage 212B (collectively referred to as "compression stages 212") includes a respective compressor 214A and 214B (collectively referred to as "compressors 214"), a respective combined condenser/static phase separator 216A and 216B (collectively referred to as "condenser/static phase separator 216"), and a respective pump 226A and 226B.

Condenser/static phase separators 216 may be configured to condense and remove water from the gas stream. Condenser/static phase separators 216 may use a variety of gravity-independent mechanisms to remove water from the gas stream. Static phase separation may include any separation mechanism that does not use moving parts, such as capillary phase separation, inertial phase separation, and vortex phase separation.

In some examples, condenser/static phase separators 216 may include capillary phase separators. Capillary phase separators may use surface tension to remove water from the gas stream. For example, capillary phase separators may have surfaces that are hydrophilic, such that the contact angle of respective polar or liquid is low, causing liquid droplets to impinge on the surfaces and stick. The surface tension of the surfaces may be sufficiently high that the liquid forms droplets on the surface to form a liquid stream. Capillary phase separators may include, but are not limited to, screen separators, wick separators, and other separators that create a sufficiently low contact angle with the liquid and/or create a sufficiently high surface tension to accumulate the liquid.

In some examples, condenser/static phase separators 216 may include inertia separators. Inertia separators may use inertia of the gas stream to remove water from the gas stream. Inertia separators that may be used include, but are not limited to, elbow separators, tee separators, and other separators that utilize a difference in fluid flow behavior between water and other constituents of the gas stream.

In some examples, condenser/static phase separators 216 may include vortex separators. Vortex separators may use momentum of the gas stream to create swirling flow, resulting in a centrifugal acceleration field that separates water from the gas stream based on differences in density.

Figure 2B:
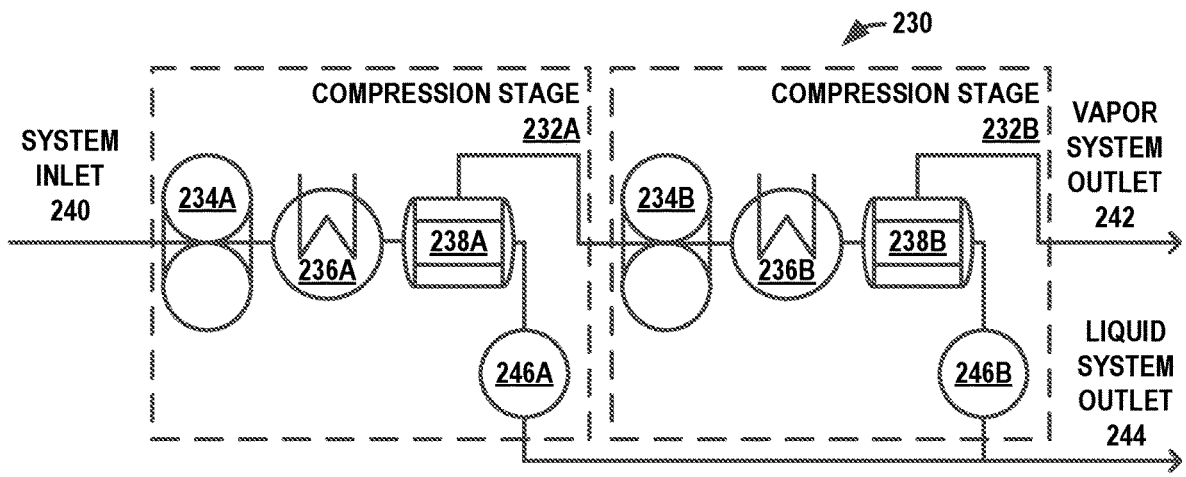
FIG. 2B is a diagram illustrating an example gas compression and component removal system for compressing a gas stream and removing a component from the gas stream using multi-stage compression and multi-stage, gravity-independent membrane phase separation.

In some examples, a gas compression and water removal system may utilize membrane phase separation to remove water from the gas stream. For example, membrane phase separation may be capable of a high degree of water removal from a gas stream, low power, and/or high reliability due to no moving parts. FIG. 2B is a diagram illustrating an example gas compression and water removal system 230 for compressing a gas stream and removing water from the gas stream using multi-stage compression and multi-stage membrane phase separation.

System 230 includes a system inlet 240, a vapor system outlet 242, a liquid system outlet 244, a first compression stage 232A, and a second compression stage 232B. Each of first compression stage 232A and second compression stage 232B (collectively referred to as "compression stages 232") includes a respective compressor 234A and 234B (collectively referred to as "compressors 234"), a respective condenser 236A and 236B (collectively referred to as "condensers 236"), a respective membrane phase separator 238A and 238B (collectively referred to as "membrane phase separators 238"), and a respective pump 246A and 246B. Condensers 236 may be configured to condense water from the gas stream and membrane phase separators 238 may be configured to remove the condensed water from the gas stream.

Figure 2C:
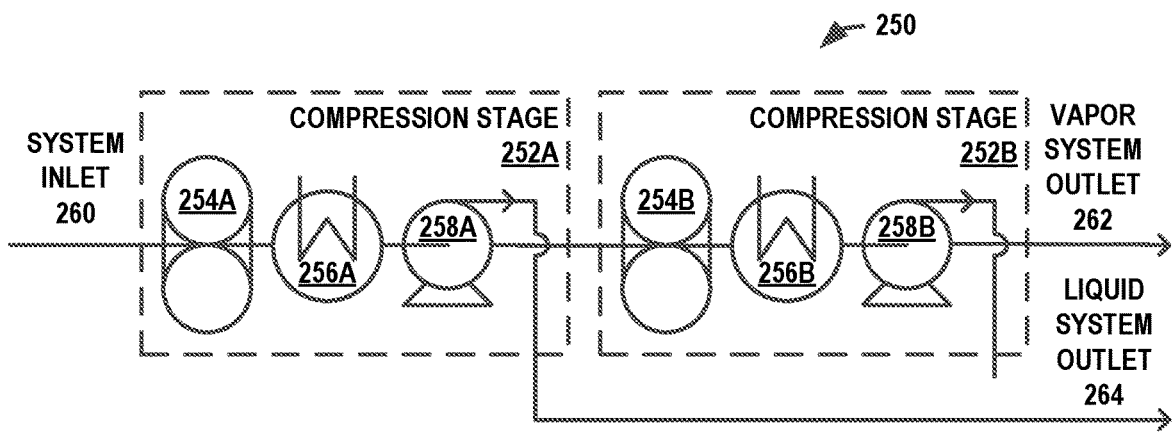
FIG. 2C is a diagram illustrating an example gas compression and component removal system for compressing a gas stream and removing a component from the gas stream using multi-stage compression and multi-stage, gravity-independent centrifugal phase separation.

Membrane phase separators 238 may use hydrophilic and/or hydrophobic membranes to remove water from the gas stream. For example, in a first mode (shown in FIG. 2B), the liquid phase may be the permeate. The gas phase may flow through the membrane, while the liquid may flow to a liquid discharge line. When the liquid is a polar liquid, membrane phase separators 238 may use hydrophobic membranes to prevent the flow of the liquid through the membrane and allow the gas to permeate. In a second mode (not shown in FIG. 2B), the gas phase may be the permeate. The gas phase may travel through the membrane without permeating, while the liquid would permeate the membrane and be carried away. In this mode, membrane phase separators 238 may use hydrophilic membranes to accomplish this separation In some examples, a gas compression and water removal system may utilize rotary phase separation to remove water from the gas stream. For example, rotary phase separation may be capable of high throughput, high degree of liquid removal, integrated pumping functionality, and/or integrated drive mechanism, such as through a common axle. FIG. 2C is a diagram illustrating an example gas compression and water removal system 250 for compressing a gas stream and removing water from the gas stream using multi-stage compression and multi-stage rotary phase separation.

System 250 includes a system inlet 260, a vapor system outlet 262, a liquid system outlet 264, a first compression stage 252A, and a second compression stage 252B. Each of first compression stage 252A and second compression stage 252B (collectively referred to as "compression stages 252") includes a respective compressor 254A and 254B (collectively referred to as "compressors 254"), a respective condenser 256A and 256B (collectively referred to as "condensers 256"), and a respective rotary phase separator 258A and 258B (collectively referred to as "rotary phase separators 258"). Condensers 256 may be configured to condense water from the gas stream and rotary phase separators 258 may be configured to remove the condensed water from the gas stream. Rotary phase separators 258 may use mechanical rotation to generate centrifugal acceleration to separate water from the gas stream. In some examples, rotary phase separators 258 may be driven by a same axis. For example, each of rotary phase separators 258 may be coupled to a common axle, such that control of rotary phase separators 258 may be simplified and/or a component weight may be reduced. In some examples, each of compressors 254 and a respective one of rotary phase separators 258 may be driven by a same axis.

Figure 3:
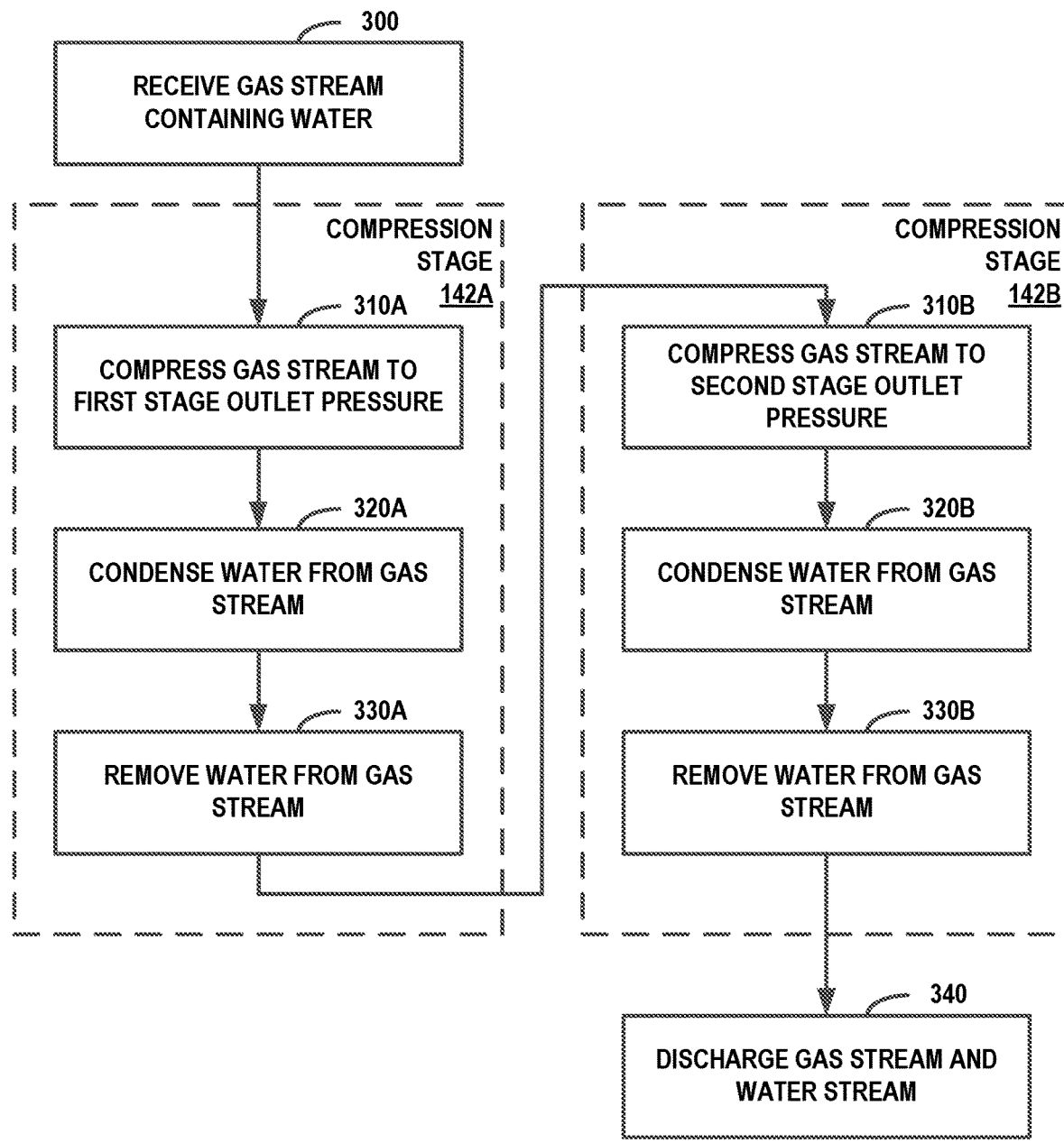
FIG. 3 is a flowchart of an example technique for compressing a gas stream and removing a component from the gas stream using multi-stage compression and multi-stage gravity-independent phase separation.

FIG. 3 is a flowchart of an example technique for compressing a gas stream and removing a component from the gas stream using multi-stage compression and multi-stage gravity-independent phase separation. The technique of FIG. 3 will be described with reference to gas compression and component removal system 106 of FIG. 1B receiving a gas stream having a first component of a gas and a second component of water; however, it will be understood that other gas compression and water removal systems, such as shown in FIGS. 2A-C, may be used to compress other gas streams and remove other components from the gas stream using multi-stage compression and gravity-independent phase separation.

The method of FIG. 3 includes receiving, by a gas compression and water removal system 106, a gas stream containing water (300). For example, controller 158 may control an inlet valve to allow the gas stream into gas compression and water removal system 106. The gas stream may contain, for example, a water concentration that is greater than approximately 20% and less than approximately 90%, such as 66%.

The method of FIG. 3 includes compressing, by a plurality of compression stages of gas compression and water removal system 106, the gas stream (310A-330B). For example, controller 158 may control the plurality of compression stages to compress the gas stream and remove water from the gas stream by sending control signals to one or more of: compressors 144 to compress the gas stream, such as to a pressure setpoint, a rotations per minute setpoint, or a volumetric flowrate setpoint; refrigeration system 160 to control a temperature of condensers 146 to condense water from the gas stream, such as to a temperature setpoint or refrigerant flowrate setpoint; phase separators 148 to remove water from the gas stream, such as to a rotational speed for a rotary phase separator; and/or pumps 156 to remove water from phase separators 148, such as to a pressure setpoint or liquid level setpoint.

For compression stage 142A, compressor 144A compresses the gas stream (310A). For example, controller 158 may send control signals to compressor 144A to cause compressor 144A to compress the gas stream, such as by controlling a compressor speed for a compressor outlet pressure setpoint, a compressor pumping speed setpoint, a compressor pressure ratio setpoint between a compressor inlet pressure and a compressor outlet pressure, and the like.

Condenser 146A receives the compressed gas stream and condenses water from the gas stream (320A). For example, controller 158 may send control signals to refrigeration system 160 to cause condenser 146A to condense water from the gas stream, such as by controlling a refrigerant flow for a refrigerant flow rate setpoint or a condenser gas stream outlet temperature setpoint, and the like.

Gravity-independent phase separator 148A receives the gas stream containing the condensed water, removes the condensed water from the gas stream, and discharges the gas stream to compressor 144B of compression stage 142B (330A). For example, for active phase separators such as rotary phase separators or passive phase separators that use pumps, controller 158 may send control signals to phase separator 148A and/or pump 156A to cause phase separators 148A to remove the water from the gas stream and discharge the gas stream, such as by controlling a rotary separator rotational speed for a rotational speed setpoint, controlling a pump speed for a pressure setpoint, and the like.

Similar to compression stage 142A, for compression stage 142B, compressor 144B compresses the gas stream (310B). Condenser 146B receives the compressed gas stream and condenses water from the gas stream (320B). Gravity-independent phase separator 148B receives the gas stream containing the condensed water, removes the condensed water from the gas stream, and discharges the gas stream to vapor system outlet 150 (330B). While not shown additional compression stages may be used. For example, if a compression ratio between a gas stream received and a gas stream discharged by gas compression and component removal system 106 is sufficiently high, a large number of compression stages may be used.

The method of FIG. 3 includes discharging, by gas compression and component removal system 106, the gas stream (340). For example, controller 158 may control an outlet valve to allow the gas stream out of gas compression and component removal system 106. The gas stream discharged by the gas compression system may include, for example, a water concentration that is less than approximately 10 weight (wt.) %, such as less than 5% for a carbon dioxide stream or less than 1% for a methane stream.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

EXAMPLES

Figure 4:
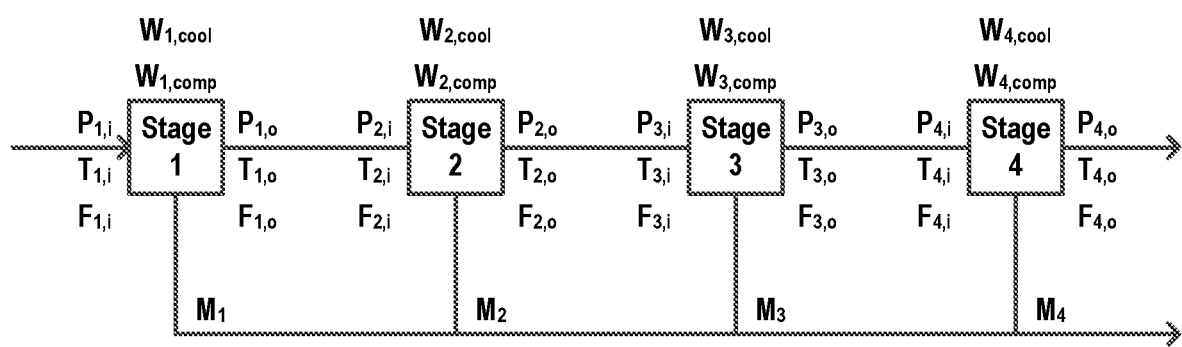
FIG. 4 is a diagram illustrating an example gas compression and water removal system for compressing a gas stream and removing water from the gas stream using four-stage compression.

FIG. 4 is a diagram illustrating an example gas compression and water removal system for compressing a gas stream and removing water from the gas stream using four-stage compression. Each stage (x) of compression receives a gas stream at an inlet pressure ($P_{x,i}$), inlet temperature ($T_{x,i}$), and inlet volumetric flow rate ($F_{x,i}$) and discharges the gas stream at an outlet pressure ($P_{x,o}$), outlet temperature ($T_{x,o}$), and outlet volumetric flow rate ($F_{x,o}$). Each stage of compression compresses the gas stream using a corresponding compression power ($W_{x,comp}$), cools the gas stream at a corresponding cooling power ($W_{x,cool}$), and removes water at a water removal flow rate ($M_x$).

The system of FIG. 4 was simulated for both an experimental example illustrating the gas compression and water removal systems discussed above, as well as a comparative example illustrating a conventional gas compression and water removal system. In the comparative example, the system of FIG. 4 was simulated for a gas compression system that only includes water removal after Stage 4. In the experimental example, the system of FIG. 4 was also simulated for a gas compression system includes water removal after each of Stages 1, 2, 3, and 4.

In both examples, the system of FIG. 4 had the following identical inlet and outlet compositions and conditions: a system inlet flowrate of 4.16 kg/day of $CO_2$ vapor and 10.45 kg/day of water vapor, a system inlet pressure of 1 torr, a system inlet temperature of 60° C., a system inlet volumetric flow rate of 9765 LPM, and system inlet water concentration of 72 wt. %; a vapor system outlet flowrate of 4.16 kg/day $CO_2$ vapor with less than 3 wt. % water vapor, a vapor system outlet pressure of 536 torr, a vapor system outlet temperature of 10° C., a vapor system outlet volumetric flow rate of 2.3 LPM; a liquid system outlet flowrate of approximately 10.45 kg/day liquid water. The compressor efficiency was assumed to be 80% per compressor, while the pressure drop per compression stage was assumed to be 3%.

The various operating parameters of the comparative example are shown in Table 1 below:

TABLE 1

| Parameter | Stage 1 | Stage 2 | Stage 3 | Stage 4 |
|---|---|---|---|---|
| Inlet Pressure (torr) | 1.0 | 4.8 | 22.5 | 108.1 |
| Outlet Pressure (torr) | 5.0 | 23.2 | 111.4 | 536.2 |
| Inlet Temperature (° C.) | 60 | 80 | 80 | 80 |
| Outlet Temperature (° C.) | 249.2 | 278.5 | 278.6 | 278.6 |
| Inlet Flow Rate (LPM) | 9765 | 2218 | 461 | 96 |
| Outlet Flow Rate (LPM) | 3085 | 698 | 145 | 30 |
| Compression Power (W) | 52.8 | 55.9 | 55.9 | 55.8 |
| Cooling Power (W) | −47.4 | −55.9 | −56.0 | −388.2 |
| Water Removal (g/min) | 0.00 | 0.00 | 0.00 | 7.27 |

The various operating parameters of the experimental example are shown in Table 2 below:

TABLE 2

| Parameter | Stage 1 | Stage 2 | Stage 3 | Stage 4 |
|---|---|---|---|---|
| Inlet Pressure (torr) | 1.0 | 4.7 | 22.5 | 108.1 |
| Outlet Pressure (torr) | 4.8 | 23.2 | 111.4 | 536.0 |
| Inlet Temperature (° C.) | 60 | 10 | 10 | 10 |
| Outlet Temperature (° C.) | 245.0 | 171.3 | 156.1 | 150.2 |
| Inlet Flow Rate (LPM) | 9765 | 1778 | 76 | 11 |
| Outlet Flow Rate (LPM) | 3156 | 580 | 24 | 4 |
| Compression Power (W) | 51.6 | 44.0 | 8.9 | 6.5 |
| Cooling Power (W) | −65.0 | −334.2 | −29.5 | −9.4 |
| Water Removal (g/min) | 0.00 | 6.72 | 0.48 | 0.07 |

The total power and total heat rejection between the comparative example and the experimental example were compared, as shown in Table 3 below:

TABLE 3

| Parameter | Comparative Example | Experimental Example | Reduction |
|---|---|---|---|
| Total Power (W) | 220.4 | 111.0 | ~50% |
| Total Heat Rejection (W) | 547.5 | 438.1 | ~20% |

As seen in Table 3 above, the system of the experimental example, which includes water removal at each of four stages using gravity-independent phase separators, had about a 50% reduction in total power and about a 20% reduction in heat rejection. As such, the system of the experimental example may require less power, have a smaller size (e.g., through smaller volumetric capacity), and operate at a lower temperature than the system of the comparative example in which water is not removed at each stage.

Various examples have been described. These and other examples are within the scope of the following claims.

What is claimed is:

1. A gas compression system, comprising:
   a system inlet configured to receive a gas stream containing a first component and a second component;
   a vapor system outlet configured to discharge the gas stream;
   a plurality of compression stages coupled in series between the system inlet and the vapor system outlet, wherein each of the plurality of compression stages comprises:
      a compressor configured to receive the gas stream from either the system inlet or another of the plurality of compression stages and compress the gas stream;
      a condenser coupled to the compressor, the condenser configured to condense the second component from the gas stream; and
      a gravity-independent phase separator coupled to the condenser, the gravity-independent phase separator configured to remove the second component from the gas stream and discharge the gas stream to either the vapor system outlet or another of the plurality of compression stages; and
   a controller configured to operate the plurality of compression stages to remove the second component from the gas stream, wherein the second component comprises water, and wherein a concentration of the water in the gas stream received at the system inlet is greater than approximately 20 wt. %.

2. The system of claim 1, wherein the gravity-independent phase separator of each of the plurality of compression stages comprises at least one of a static phase separator, a capillary phase separator, an inertial phase separator, a vortex phase separator, a membrane phase separator, a centrifugal phase separator, or a rotary phase separator.

3. The system of claim 2, wherein the gravity-independent phase separator comprises the rotary phase separator, and wherein the rotary phase separator for each compression stage is driven by a common axle.

4. The system of claim 3, wherein the compressor and the gravity-independent phase separator for each compression stage are driven by the common axle.

5. The system of claim 1, further comprising a liquid system outlet configured to discharge the second component removed from each phase separator.

6. The system of claim 1, wherein the gravity-independent phase separator of each of the plurality of compression stages is coupled to a liquid discharge line and configured to discharge the second component from the gas stream to the liquid discharge line, and wherein each of the plurality of compression stages further comprises a pump coupled to the liquid discharge line, the pump configured to discharge the second component from the liquid discharge line.

7. The system of claim 1, wherein the condenser and the gravity-independent phase separator of each compression stage are integrated into a single unit.

8. The system of claim 1, wherein the compressor for each compression stage is driven by a common axle.

9. The system of claim 1, wherein each condenser comprises one or more cooling jackets thermally coupled to at least one of the compressor or the gravity-independent phase separator of the respective compression stage.

10. The system of claim 1, wherein a concentration of water in the gas stream discharged by the system is less than approximately 10 wt. %.

11. A method, comprising:
   receiving, by a system inlet of a gas compression system, a gas stream containing a first component and water, wherein a concentration of the water in the gas stream received at the system inlet is greater than approximately 20 wt. %;
   compressing, by a plurality of compression stages of the gas compression system, the gas stream; and
   discharging, by a vapor system outlet of the gas compression system, the gas stream,
   wherein the compression stages of the plurality of compression stages are coupled in series between the system inlet and the vapor system outlet, and
   wherein each of the plurality of compression stages comprises:
      a compressor for compressing the gas stream;
      a condenser coupled to the compressor for condensing the water from the gas stream;
      a gravity-independent phase separator coupled to the condenser for removing the water from the gas stream and discharging the gas stream.

12. The method of claim 11, wherein the plurality of compressions stages of the gas compression system compresses the gas stream in at least one of a microgravity environment, a partial or low gravity environment, a high gravity environment, or a turbulent environment.

13. The method of claim 11, wherein each gravity-independent phase separator comprises at least one of a static phase separator, a capillary phase separator, an inertial phase separator, a vortex phase separator, a membrane phase separator, a centrifugal phase separator, or a rotary phase separator.

14. The method of claim 11, wherein the gas compression system receives the gas stream at a pressure less than approximately 100 torr and discharges the gas stream at a pressure less than approximately 10,000 torr.

15. The method of claim 11, wherein the first component comprises one of carbon dioxide and methane.

16. The method of claim 11, wherein a concentration of water in the gas stream discharged by the gas compression system is less than approximately 10 wt. %.

17. The method of claim 11, wherein a ratio of a water concentration of the gas stream received by the gas compression system to a water concentration of the gas stream discharged by the gas compression system is greater than approximately 10.

18. The method of claim 11, wherein the first component comprises carbon dioxide, and wherein the method further comprises reacting the carbon dioxide with hydrogen gas to form methane.

19. The method of claim 18, further comprising compressing, by a second plurality of compression stages of the gas compression system, the methane in a methane stream, wherein each of the second plurality of compression stages comprises:
   a compressor for compressing the methane stream;
   a condenser coupled to the condenser for condensing water from the methane stream;
   a gravity-independent phase separator coupled to the condenser for removing the water from the methane stream and discharging the methane stream.

20. A system, comprising:
a carbon dioxide and water removal system configured to remove carbon dioxide and water from a cabin of a spacecraft, wherein the carbon dioxide and water removal system includes one or more membrane separators; and
a gas compression system comprising:
- a system inlet configured to receive a gas stream containing carbon dioxide and water from the one or more membrane separators;
- a vapor system outlet configured to discharge the gas stream; and
- a plurality of compression stages coupled in series between the system inlet and the vapor system outlet, wherein each of the plurality of compression stages comprises:
  - a compressor configured to receive the gas stream from either the system inlet or another of the plurality of compression stages and compress the gas stream;
  - a condenser coupled to the compressor, the condenser configured to condense water from the gas stream; and
  - a gravity-independent phase separator coupled to the condenser, the gravity-independent phase separator configured to remove water from the gas stream and discharge the gas stream to either the vapor system outlet or another of the plurality of compression stages.

* * * * *